(12) United States Patent
Hendriks et al.

(10) Patent No.: US 11,617,666 B2
(45) Date of Patent: Apr. 4, 2023

(54) PROSTHESIS

(71) Applicant: GYROMOTICS HOLDING B.V., Delft (NL)

(72) Inventors: Guido Jérôme Hendriks, Delft (NL); Jacob Leonard Roggeveen, Delft (NL); Iris Eline Ritsma, Delft (NL); Thomas Sebastiaan Zwart, Delft (NL); Francis Folkers, Delft (NL); Stijn Jagers Op Akkerhuis, Delft (NL); Clément Aart Ijje Heinen, Delft (NL); Donovan Dane Lester Lewis, Delft (NL)

(73) Assignee: GYROMOTICS HOLDING B.V., Delft (NL)

( * ) Notice: Subject to any disclaimer, the term of this patent is extended or adjusted under 35 U.S.C. 154(b) by 386 days.

(21) Appl. No.: 16/769,268

(22) PCT Filed: Dec. 7, 2018

(86) PCT No.: PCT/NL2018/050823
§ 371 (c)(1),
(2) Date: Jun. 3, 2020

(87) PCT Pub. No.: WO2019/112435
PCT Pub. Date: Jun. 13, 2019

(65) Prior Publication Data
US 2020/0289293 A1   Sep. 17, 2020

(30) Foreign Application Priority Data
Dec. 7, 2017  (NL) .................................... 2020034

(51) Int. Cl.
*A61F 2/66* (2006.01)

(52) U.S. Cl.
CPC .............. *A61F 2/66* (2013.01); *A61F 2/6607* (2013.01); *A61F 2002/665* (2013.01);
(Continued)

(58) Field of Classification Search
CPC .. A61F 2/66; A61F 2/6607; A61F 2002/6614; A61F 2002/6642;
(Continued)

(56) References Cited

U.S. PATENT DOCUMENTS

| 5,139,525 A | 8/1992 | Kristinsson |
| 11,311,393 B2 * | 4/2022 | Sampson .................. A61F 2/78 |

(Continued)

FOREIGN PATENT DOCUMENTS

WO  2017049234 A1  3/2017

OTHER PUBLICATIONS

International Search Report and Written Opinion for the International Patent Application No. PCT/NL2018/050823, dated Apr. 4, 2019, 8 pages.

*Primary Examiner* — Bruce E Snow
(74) *Attorney, Agent, or Firm* — KDB Firm PLLC

(57) ABSTRACT

A joint for a prosthesis comprises a prosthesis part and a body part. The two parts are connected by a connection part. A first pair of engaging sets of abutments is provided on the connection part and the prosthesis part and a second pair of engaging sets of abutments is provided on the connection art and the body part. By adjusting position of the connection part, the first pair of sets are disengageable and by further adjusting the position, the second pair of sets are also disengageable. This allows for adjustment of the joint at two levels. A prosthesis includes two stripes of resilient material of which at least one has a curved part and a straight part.

(Continued)

The joint is provided at a distal end, at the concave part of the strips. At straight parts, the strips cross and one strip extends beyond the other.

17 Claims, 5 Drawing Sheets

(52) U.S. Cl.
CPC .............. *A61F 2002/6614* (2013.01); *A61F 2002/6642* (2013.01); *A61F 2002/6664* (2013.01); *A61F 2002/6671* (2013.01)

(58) Field of Classification Search
CPC ........ A61F 2002/665; A61F 2002/6664; A61F 2002/6671
See application file for complete search history.

(56) References Cited

U.S. PATENT DOCUMENTS

| | | | |
|---|---|---|---|
| 2020/0289293 A1* | 9/2020 | Hendriks | A61F 2/68 |
| 2020/0375764 A1* | 12/2020 | Clausen | A61F 2/6607 |

* cited by examiner

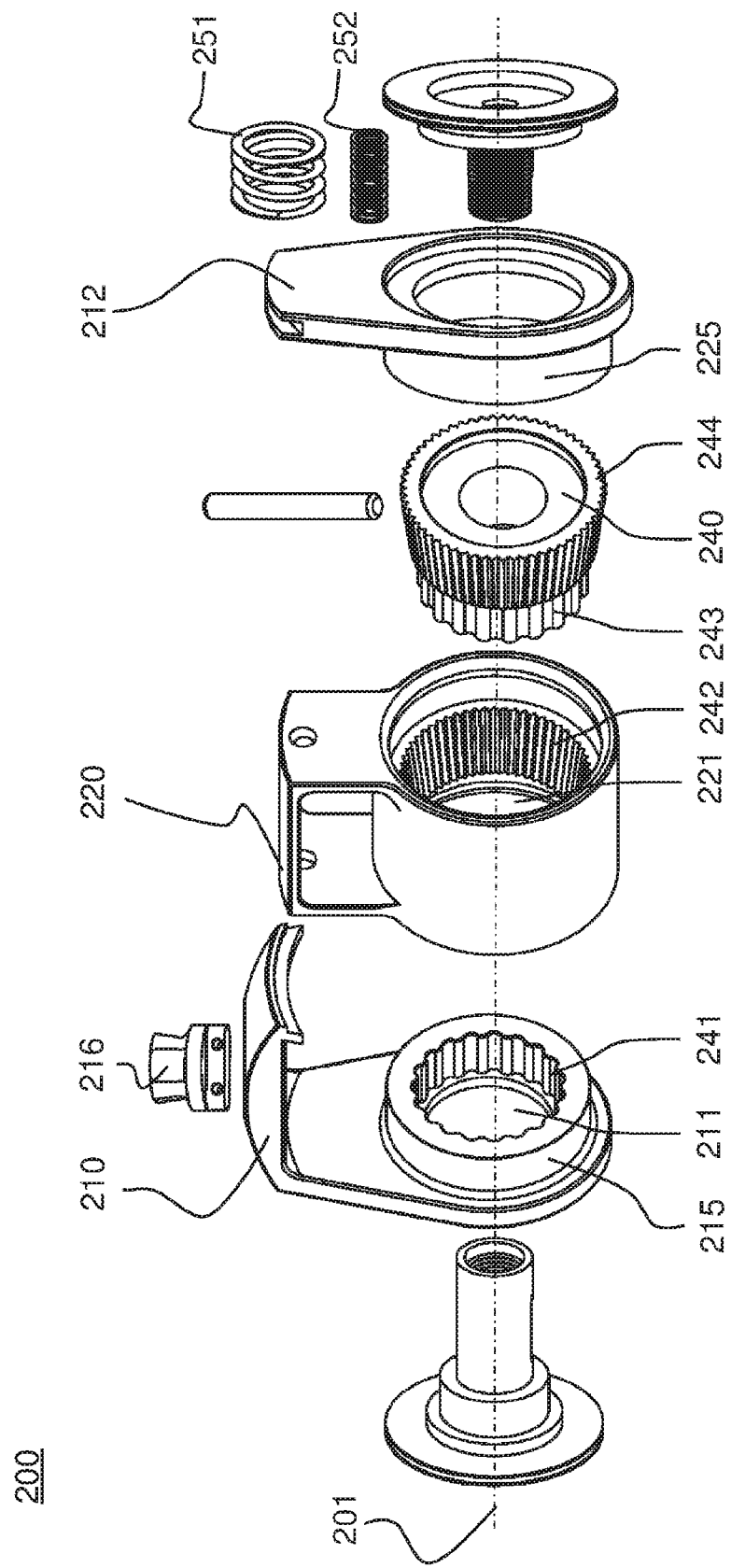

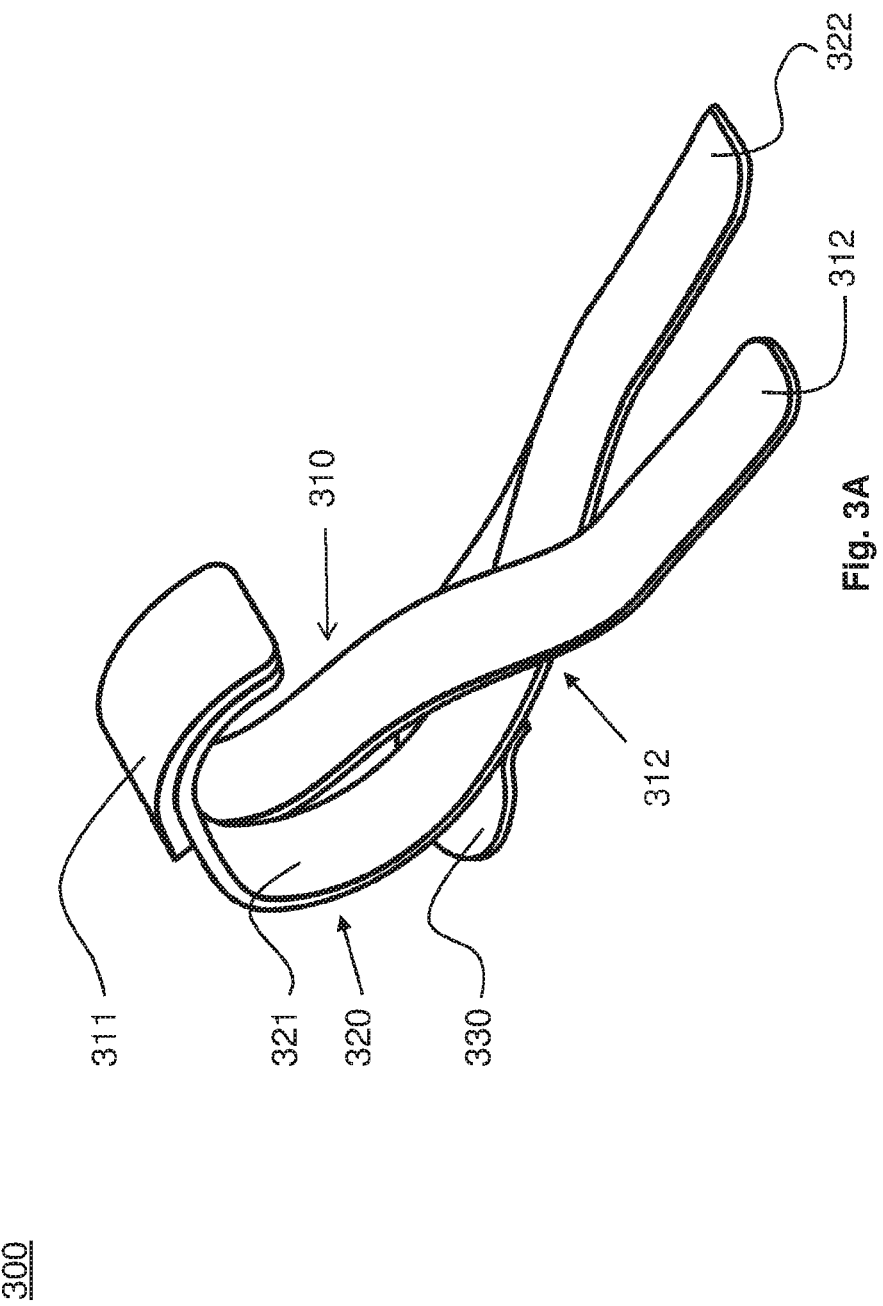

PROSTHESIS

TECHNICAL FIELD

The invention relates to the field of prostheses, and more specifically to foot and ankle prostheses.

BACKGROUND

Prostheses are provided for many different body parts in many different form factors. Prostheses may comprise passive components, such as springs and dampers, but also active components, such as actuators.

WO2017171104 discloses an artificial foot.

SUMMARY

Known prosthesis are complex to adjust in view of the various components. Prostheses that are less complex exist, but such prostheses have less option for adjustment. It is preferred to provide a prosthesis that provides more flexibility.

A first aspect provides a joint for a prosthesis. The joint comprises a body joint part, a prosthesis joint part, arranged to be connected to a prosthesis and to rotate relative to the body joint part around an axis of rotation and a connection part, arranged to connect the body joint part and the prosthesis joint part. In this joint, a first of the body joint part and a first side of the connection part is provided with a first set of abutments with a first periodicity and a first of the prosthesis joint part and a second side of the connection part is provided with a second set of abutments with a second periodicity. Furthermore, a second of the body joint part and the first side of the connection part is provided with a third set of abutments arranged to engage with abutments of the first set of abutments, a second of the prosthesis joint part and a second side of the connection part is provided with a fourth set of abutments arranged to engage with abutments of the second set of abutments; and the connection part is arranged to be translated between a first position, a second position, and a third position. In the first position, at least a part of the third set of abutments engages with at least a part of the first set of abutments and at least a part of the fourth set of abutments engages with at least a part of the second set of abutments. In the second position, at least a part of the third set of abutments engages with at least a part of the first set of abutments and the fourth set of abutments does not engage with the second set of abutments. In the third position the third set of abutments does not engages with the first set of abutments; and the fourth set of abutments does not engage with the second set of abutments.

Providing two groups of pairs of engaging abutments, a high degree of freedom of a position of the angle of the body joint part and the prosthesis joint part may be provided, even though both groups comprise a limited amount of abutments.

In case adjustment in a relatively small amount [number] of steps with a coarse resolution is sufficient for a particular adjustment, the connection part may be moved to the second position.

In an embodiment, the body joint part is provided with a first opening, the prosthesis joint part is provided with a second opening, the first opening and the second opening are aligned on the axis of rotation and the connection part is substantially cylindrical, and is arranged to at least be provided in the second opening.

Such embodiment allows the connection part to function as an axle for the joint.

In another embodiment, the first set of abutments is provided in the first opening of the body joint part, the second set of abutments is provided in the second opening of the prosthesis joint part; and the third set of abutments and the fourth set of abutments are provided on an outside of the connection part. This embodiment allows to engage and disengage pairs of sets of abutments by translating the connection part to the various positions.

In a further embodiment, at least one of the first set of abutments and the second set of abutments is conically shaped, conically such that an outside diameter increases in the direction of the first position and at least one of the third set of abutments and the fourth set of abutments is conically shaped, conically such that an outside diameter decreases in the direction of the first position.

In this embodiment, the first of the first and second set of abutments does not have to be fully disaligned with a first of the third and the fourth set of abutments. If the mating conical parts are moved apart from one another, the abutments on these parts will disengage already when the sets of abutments still partially overlap.

Yet another embodiment comprises a first urging element with a first stiffness, arranged to urge the connection part into the first position. This allows to securely lock the connection part in the first position upon release.

Again a further embodiment comprises a second urging element with a second stiffness, arranged to urge the connection part into the second position, wherein the first stiffness is lower than the second stiffness. This embodiment allows for moving the connection part from the first position to the second position with little effort for quick adjustments. For making finer adjustments by moving the connection part from the second to the third position, more effort is required. This improves detecting a selection between the second and third position.

In yet a further embodiment, the first periodicity and the second periodicity have no common denominator larger than 1. Such embodiment allows for the highest possible of steps for adjustment, the number of abutments of the first periodicity multiplied by the number of abutments of the second periodicity.

A second aspect provides a prosthesis comprising a joint according to the first aspect. In this prosthesis, the body joint part is connected to a leg connection, the prosthesis joint part is arranged to be connected to a foot prosthesis and the foot prosthesis comprising a first curved strip. The first curved strip comprises a first curved section and a first straight section, at a proximal end provided to the first curved section. In this prosthesis, the foot prosthesis is arranged to be connected at a concave side of the first curved section to the prosthesis joint part; and the foot prosthesis is arranged to bend resiliently.

An embodiment further comprises a second curved strip, comprising a second curved section and a second straight section at a proximal end provided to the second curved section. In this embodiment, the second curved section at a concave side is connected to a convex side of the first curved section, the second curved section crosses the first curved section at a crossing substantially at respectively a transition of the second curved section into the second straight section and a transition of the first curved section into the first straight section and a distal end of the first straight section and a distal end of the second straight section protrude substantially parallel.

This embodiment allows for improved mimicking dynamics of a natural foot and the inversion/eversion in particular.

In another embodiment, the distal end of the first straight section protrudes further than the distal end of the second straight section. This embodiment allows for mimicking a large toe.

Whereas the embodiments of the second aspect provide examples for use of the first aspects and embodiments thereof, at least some embodiments provide basis for an aspect in itself, for use with another type of joint.

BRIEF DESCRIPTION OF THE DRAWINGS

The various aspects and embodiments will now be discussed in conjunction with drawings. In the drawings:

FIG. 3A shows a foot prosthesis; and

DETAILED DESCRIPTION

Figure 1:
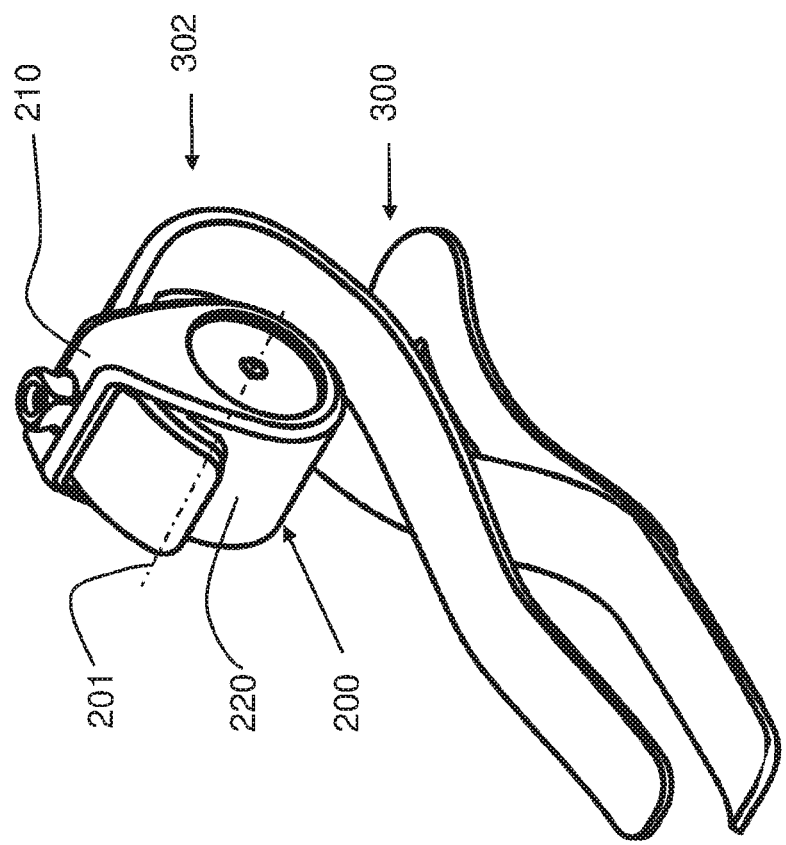
FIG. 1 shows a prosthesis.

FIG. 1 shows a prosthesis 100, comprising a joint 200, a body joint part 210, a prosthesis joint part 220, and a foot prosthesis 300. The foot prosthesis 300 is arranged to be connected to the prosthesis joint part 220, and to rotate relative to the body joint part 210 over a rotation axis 201. The joint 200 is arranged to allow the rotation of the body joint part 210 relative to the prosthesis joint part 220.

The foot prosthesis 300 may comprise a curved section 302, of which a concave part is attached to the prosthesis joint part 220. With the concave part of the foot prosthesis 300 being attached to the prosthesis joint part 220, the total volume occupied by the prosthesis 100 is relatively small, while providing resilience by virtue of the relatively large curved section 302. Furthermore, when the prosthesis 300 is used as an ankle prosthesis, the attachment to the concave part of the foot prosthesis 300 provides a natural point of rotation, corresponding to the natural position of the ankle relative to the foot and a leg.

While FIG. 1 shows a prosthesis 100 for a foot and an ankle, in other envisioned embodiments, the prosthesis 100 may be arranged to substitute for any other body part, such as a shoulder, elbow, wrist, finger, knee, hip or any other body part.

Figure 2:
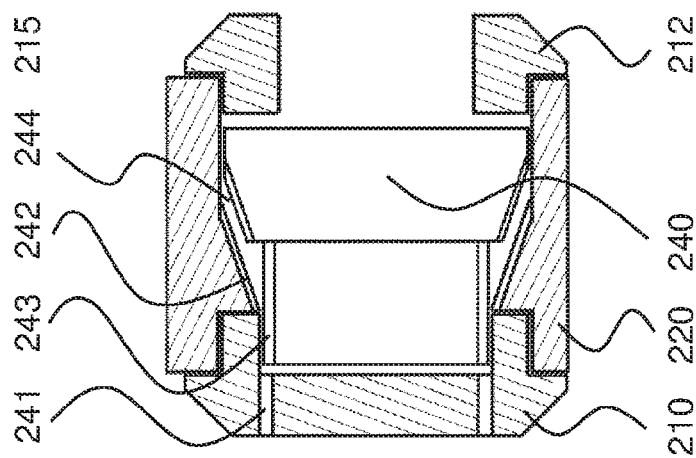
FIG. 2A shows an exploded view of a joint.
FIG. 2B shows a cross-section with a connection part in a first position.
FIG. 2C shows a cross-section with the connection part in a second position
FIG. 2D shows a cross-section with the connection part in a third position.
Figure 2:
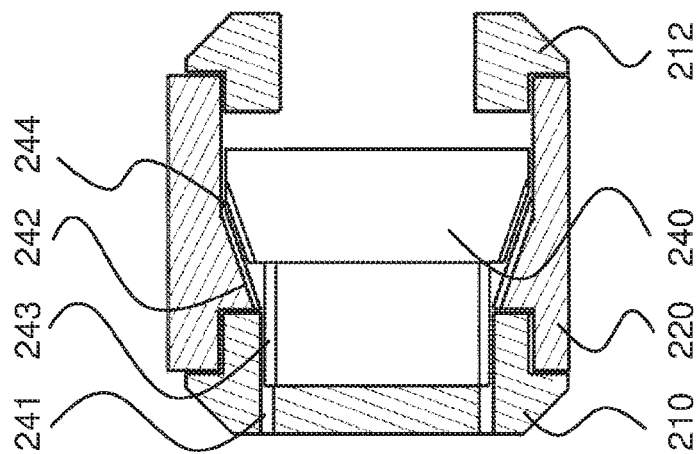
Figure 2:
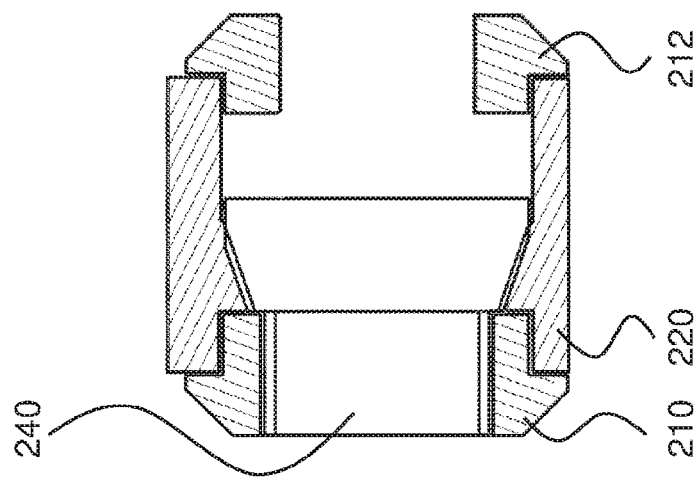

FIG. 2A shows an embodiment of the joint 200, comprising the body joint part 210, the prosthesis joint part 220 and the connection part 240. The connection part 240 is arranged to connect the body joint part 210 and the prosthesis joint part 220. The connection part 240 may be provided substantially axisymmetric around the axis of rotation 201.

The body joint part 210 is provided with a connection element 216 to provide a connection with a body part. The connection element 216 may be at least part of a male or female pyramid adapter, tube clamp, 4 hole adapter, any other prosthetics connector, or any combination thereof.

In an embodiment of the joint 200, the connection part 240 is arranged to temporarily allow a rotation between the body joint part 210 and the prosthesis joint part 220 over the rotation axis 201. To allow the rotation, a user interaction with the prosthesis 100 is required. Such an interaction may be used to permanently or temporarily lock or unlock the rotation, or any combination thereof. The user interaction may be performed by pressing a button, rotating a knob, pulling a lever, or any other user interaction. Alternatively or additionally, the translating of the connection part 240 may be effectuated by means of an actuator like an electromotor, either rotational or linear. The locking of the rotation may either be caused be a force closed mechanism using for example friction elements or a form closed mechanism based on for example engaging abutments provided by cams, recesses and other deformations of, on or in a surface.

In another embodiment of the joint 200, a first of the body joint part 210 is provided with a first set of abutments 241 with a first periodicity. A first side of the connection part 240 is provided with a third set of abutments 243 with the first periodicity. A first of the prosthesis joint part 220 is provided with a second set of abutments 242 with a second periodicity. A second side of the connection part 240 is provided with a fourth set of abutments 244 with the second periodicity. The third set of abutments 243 is arranged to abut to abutments from the first set of abutments 241. The fourth set of abutments 244 is arranged to abut to abutments from the second set of abutments 242.

In an embodiment of the joint 200, the connection part 240 is arranged to be moved between a first position, a second position, and a third position by translating the connection part 240 over the rotation axis 201. In the first position, at least a part of the third set of abutments 243 engages with at least part of the first set of abutments 241 and at least a part of the fourth set of abutments 244 engages with at least part of the second set 242 of abutments. This is depicted by FIG. 2B.

In the second position, at least a part of the third set of abutments 243 engages with at least part of the first set of abutments 241, and the fourth set of abutments 244 does not engage with the second set of abutments 242. This is depicted by FIG. 2C. It is noted that by virtue of the conical part of the connection element on which the fourth set of abutments 244 is provided, the fourth set of abutments 244 and the second set of abutments 242 disengage already at the second position of the connection element 240, while the first set of abutments 241 and the third set of abutments 243 are still engaged.

In the third position, the third set of abutments 243 does not engage with the first set of abutments 241, and the fourth set of abutments 244 does not engage with the second set of abutments 242. This is depicted by FIG. 2D.

When placed in the first position, the connection part 240 connects the body joint part 210 and the prosthesis joint part 220 such that the body joint part 210 and the prosthesis joint part 220 are not able to rotate relative to each other over the axis of rotation 201. This is established by the first set of abutments 241 on the body joint part 210 engaging with the third set of abutments 243 on the connection part 240 on one hand and the second set of abutments 242 engaging with the fourth set of abutments 244 on the connection part. In this way, the connection part 240 provides a substantially rigid connection between the body joint part 210 and the prosthesis joint part 210.

When placed in the second position, the connection part 240 is connected with the body joint part 210 such that the rotation of the connection part 240 over the axis of rotation 201 is coupled to the rotation of the body joint part 210 over the axis of rotation 201. Worded differently, the connection part 240 and the body joint part 210 are rigidly—yet realisably connected to one another. However, in this position, the prosthesis joint part 220 is allowed to rotate freely over the axis of rotation 201 relative to the connection part 240 that is rigidly coupled to the body joint part 210, as the applicable abutments do not engage.

When the connection part 240 is placed in this second position, the user of the prosthesis is allowed to place the prosthesis joint part 220 at an angle relative to the body joint part 210 with a resolution corresponding to the first periodicity. When the desired angle is set, the connection part 240 may be set back to the first position. This position allows for quick adjustment of an angle between the body joint part 210 and the prosthesis joint part 220.

When placed in the third position, the connection part 240 is neither rigidly connected to the body joint part 210, or to the prosthesis joint part 220. In such a configuration, the connection part 240, the body joint part 210 and the prosthesis joint part 220 are all allowed to rotate freely relative to each other. When the connection part 240 is placed in this third position, the user of the prosthesis is allowed to place the prosthesis joint part 220 at an angle relative to the body joint part 210 with a resolution corresponding to the first periodicity—number of first abutments 241—times the second periodicity—number of second abutments 242, provided that the first periodicity and the second periodicity have no common denominator larger than one. When the desired angle is set, the connection part 240 may be set back to the first position in which applicable abutments engage as discussed above.

The ability to place the connection part 240 in the first position, the second position, and the third position allows the user to set the angle between the prosthesis joint part 220 and the body joint part 210 with a large resolution or a small resolution, respectively in the second position and the third position of the connection part 240.

The first set of abutments 241, the second set of abutments 242, the third set of abutment 243, and the fourth set of abutments 244 may comprise any number of abutments, including only one abutment. It is noted that if the first set of abutments 241 comprises only one abutment, the third set of abutments 243 comprises more than one abutment—and vice versa. If the second set of abutments comprises only one abutment, the fourth set of abutments 244 comprises more than one abutment—and vice versa. In a preferred embodiment of the joint 200, the first periodicity and the second periodicity have no common denominator larger than one, wherein said common denominator is an integer. This allows a more accurate setting of the angles of the prosthesis joint part 220 relative to the body joint part 210.

For example, whereas a first periodicity of 2 and a second periodicity of 8 only gives 8 possible angles for the prosthesis joint part 220 relative to the body joint part 210, a first periodicity of 2 and a second periodicity of 7 gives 14 possible angles for the prosthesis joint part 220 relative to the body joint part 210. In further envisioned embodiment, 50, 250, 500 or even more possible angles are envisioned with corresponding first periodicity and second periodicity, allowing accurate setting of the angle between the body joint part 210 and the prosthesis joint part 220. In an embodiment of the joint 200, the first periodicity is smaller than the second periodicity. In another embodiment of the joint 200, the first periodicity is larger than the second periodicity. A first periodicity of 19 and a second periodicity of 58 are preferred; this means that at least one of the first set of abutments 241 and the third set of abutments 243 comprises 19 teeth and that at least one of the second set of abutments 242 and the fourth set of abutments 244 comprises 58 teeth or cams.

Optionally, the joint 200 may be provided with a first urging element 251. Herein, the first urging element 251 is arranged to urge the connection part 240 towards the first position. As a further option, alternatively or additionally, the joint 200 may be provided with a second urging element 252. The second urging element 252 is arranged to urge the connection part 240 toward the second position. A first stiffness of the first urging element 251 is preferably lower than a second stiffness of the second urging element 252. This difference in stiffness may be of an order such as 2, 5, 10 or even higher. The difference in stiffness allows the user of the prosthesis 300 to more easily position the connection part 240 in a desired position. This desired position is preferably the second position for a large resolution setting of the angle. Alternatively, it is the third position for a small resolution setting of the angle between the body joint part 210 and the prosthesis joint part 220.

The first urging element 251 and the second urging element 252 may be provided as a coil spring, helical spring, Belleville washer, any other urging element, or any combination thereof.

In another embodiment of the joint 200, the body joint part 210 comprises a first opening 211, and the prosthesis joint part 220 comprises a second opening 221. The first opening 211 and the second opening 221 are substantially axisymmetric provided around the axis of rotation 201 and are thus in register relative to one another. In this embodiment, the connection part 240 is arranged to be provided at least partially in the second opening 221, and optionally at least partially in the first opening 211.

In an embodiment of the joint 200, the first set of abutments 241 is provided on an inside of the first opening 211, the second set of abutments 242 is provided on an inside of the second opening 221. The third set of abutments 243 and the fourth set of abutments 244 are provided on an outside of the connection part 240.

In yet another embodiment of the joint 200, at least a part of the connection part 240 on which one of the first set of abutments 241 and the second set of abutments 242 is provided is conically shaped, wherein an outside diameter of connection element, with the abutments, increases towards the first position. Also, at least one of the third set of abutments 243 and the fourth set of abutments 244 are conically shaped, wherein an outside diameter of the abutments decreases towards the first position. In such an embodiment, the distance between the first position and the second position can be kept small, whilst keeping the contact area between the set of conical abutments large.

In the embodiment shown by FIG. 2A, the part of the connection part 240 on which the fourth set of abutments 244 is provided tapers to a smaller diameter closer to the third set of abutments 243. The second set of abutments 242 provided in the second opening 221 tapers in a complementary form, such that when the connection part 240 is provided in the second opening 221 such that the third set of protrusions 243 protrudes from the prosthesis joint part 220, the second set of protrusions 242 engages with the fourth set of protrusions 244. An advantage of these tapered shapes is that the connection part 240 does not have to be translated such that the fourth set of abutments 244 is fully placed beyond the second set of abutments 242. By virtue of the conical shapes of the sets of abutments, the abutments disengage already after a partial displacement of the second set of abutments 242 relative to the fourth set of abutments 244.

In a further embodiment of the joint 200, the joint is provided with a second body joint part member 212. The second body joint part member 212 is arranged to constrain the axial translation of the connection part 240. To this effect, the second body joint part member 212 may be rigidly connected to the body joint part 210.

The body joint part 210 may be provided with a first alignment abutment 215, arranged to align the prosthesis joint part 212 relative to the body joint part 210, such that a centre line of the body joint part 210 and a centre line of the prosthesis joint part 212 are aligned with the axis of rotation 201. Preferably, the first opening 211 is aligned with the second opening 221. In an embodiment of the joint 200 comprising the second body joint part member 212, the second body joint part member 212 may be provided with a second alignment abutment 225 arranged to align the prosthesis joint part 212 with the second body joint part member 212 on the axis of rotation 201.

FIG. 3A shows the foot prosthesis 300, comprising a first curved strip 310, a second curved strip 320, and a heel part 330. The first curved strip 310 comprises at a proximal end a first curved section 311 and at a distal end a first straight section 312. The second curved strip 320 comprises at a proximal end a second curved section 321, and at a distal end a second straight section 322.

The first curved strip 310 is arranged to provide a resilient support between the user of the prosthesis 300 and an underground on which the user may be standing. The weight of the user on the prosthesis 300 may compress the prosthesis 300, and with the release of the weight, for example when lifting a leg during walking, the prosthesis 300 may return to a predetermined shape.

To provide the resilient support between the user of the prosthesis 300 and the underground on which the prosthesis 300 is placed, the prosthesis 300 is provided with at least the second curved strip 320, optionally the first curved strip 310, and optionally the heel part 330. A reason for this order is that the prosthesis 300 is preferred to comprise a part that acts as a big toe, like the second straight end 322 as shown in FIG. 3A. The heel part 330 may furthermore be configured such that is only provides support between the user of the prosthesis 300 and the underground when the prosthesis joint part 220 is provided in a pre-determine range of angles relative to the body joint part. When the prosthesis 300 for example is used while running, the user might not want the heel part 330 to make contact with the underground on which the user is running, either directly or indirectly. This may for example be achieved by pivoting the joint of the prosthesis 300 as discussed above.

In an embodiment of the foot prosthesis 300, the foot prosthesis 300 comprises the first curved strip 310. The first curved strip 310 is arranged to be attached to the prosthesis joint part 220 at a convex side of the first curved section 311. Due to the curved shape and in particular by virtue of resilient nature of the material of the first curved strip 310, the first curved strip 310 is arranged to bend under a load applied to a top side of the foot prosthesis 300.

In another embodiment of the foot prosthesis 300, the foot prosthesis 300 comprises the first curved strip 310 and the second curved strip 320. The second curved strip 320 comprises at the proximal end the second curved section 321, and at the distal end the second straight section 322. The second curved strip 320 is connected to a convex side of the first curved strip 310. The first curved strip 310 crosses the second curved strip 320 at a cross point 312. At this cross point 312, the first curved strip 310 may be connected to the second curved strip 320. Such connection may be fixed or, alternatively, allow for at least one of a rotational or translational movement of the first curved strip 310 relative to the second curved strip.

At a distal side of the cross point 312 the first straight section 312 and the second straight section 322 protrude towards respectively the distal end of the first straight section 312 and the distal end of the second straight section 322. In an embodiment, the first straight section 312 protrudes further than the second straight section 322. In another embodiment, the second straight section 322 protrudes further than the first straight section 312. The difference is length between the first straight section 312 and the section straight section 322, which may resemble a big toe and a small toe in a human foot, increases stability of the foot prosthesis 300. When configured for activities such as running, the user of the foot prosthesis 300 may be supported only by the straight section that protrudes the furthest.

In the embodiments of the foot prosthesis 300 that comprise the first straight section 312 and the second straight section 322, the foot prosthesis 300 is allowed to twist under torsion. This so-called eversion and inversion is allowed by the fact that the first straight section 312 and the second straight section 322 are allowed to move relative to one another, more in particular at least one of bend individually, shift relative to one another and may twist around each other at the end close to where they connect to the joint. This also increases stability for the user when walking on uneven surfaces.

When walking, a human first positions his heel on the underground. Next, the foot rolls into place and consecutively rolls further until the weight of the user is provided on the toes. To mimic such behaviour in the foot prosthesis 300, the first curved strip 310 and the optional second curved strip 320 may be provided as resilient elements, arranged to bend under a bending moment. Such a bending moment occurs when the user rolls the foot over the underground.

In yet another embodiment of the foot prosthesis 300, the foot prosthesis 300 comprises the first curved strip 310 comprising the first curved section 311 and the first straight section 312, and the second straight section 322. In this embodiment, the second straight section 322 is connected to the first curved strip 310 at a proximal end of the second straight section 322.

In another embodiment of the foot prosthesis 300, the foot prosthesis 300 comprises the first curved strip 310, the second curved strip 320, and the heel part 330. In one embodiment of the foot prosthesis 300, the heel part 330 is at a first end connected to the first curved strip 310. In another embodiment of the foot prosthesis 300, the heel part 330 is connected at a second end to the second curved strip 310. In yet another embodiment of the foot prosthesis 300, the heel part 330 is at the first end connected to the first curved strip 310 and at the second end connected to the second curved strip 320.

The first curved strip 310 and the second curved strip 320 comprises a resilient material, arranged to return to a predetermined shape after a load has been applied and released again. The material may be a plastic, carbon fibre, titanium, another metal, a resin, any other material or any combination thereof, for example in the form of a composite.

In yet another embodiment, the first curved strip 310 and the second curved strip 320 are manufactured as a single part. Furthermore, the first curved strip 310, the second curved strip 320, and the heel part 330 may be manufactured as a single part. Also, any other combination of two of the first curved strip 310, the second curved strip 320 and the heel part 330 may be manufactured as a single part. The single part or multiple parts may be manufactured by means of for example 3D printing, moulding, any other manufacturing method or any combination thereof.

Figure 3B:
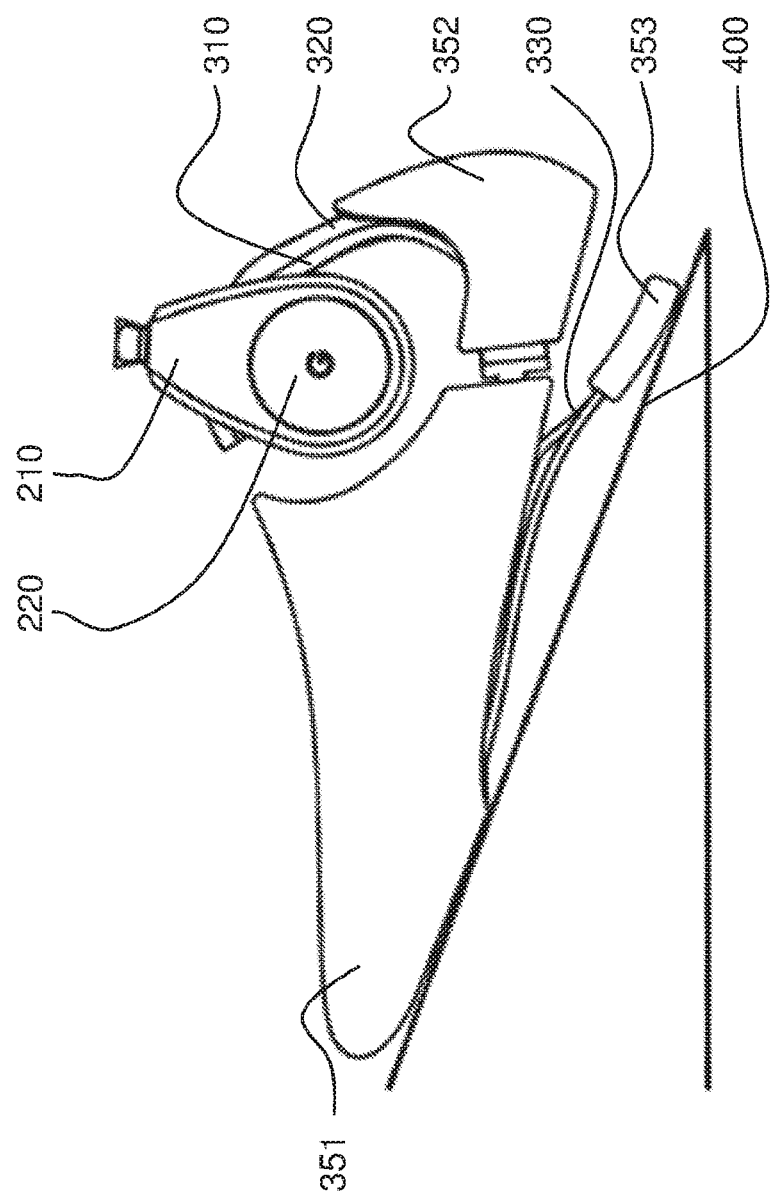
FIG. 3B shows the foot prosthesis with moulds.

FIG. 3B shows the prosthesis 100, further comprising a foot mould 351, a heel mould 352 and a sole mould 353. The foot mould 351 may be attached to at least one of the first curved strip 310 and the second curved strip 320.

In FIG. 3B, the prosthesis 100 is placed on inclined surface 400. The angle of the prosthesis joint part 220 relative to the body joint part 210 is in this configuration chosen such that the prosthesis allows the user to walk as comfortably as possible uphill.

The prosthesis 100 as shown in FIG. 3B is provided with the foot mould 351, the heel mould 352, and the sole mould 353. However, other embodiments are also envisioned with only one or two of the foot mould 351, the heel mould 352, and the sole mould 353.

At least one of the foot mould 351, the heel mould 352, and the sole mould 353 may be provided interchangeably, to change the look or performance of the foot prosthesis 300. For example, when used during swimming, the foot mould 351 which in a first configuration resembles the shape of a foot may be interchanged with a foot mould 351 that resembles the shape of a diving flipper.

Further configurations of the angle between the prosthesis joint part 220 relative to the body joint part 210 are also envisioned. These configurations may correspond to walking, running, jogging walking downhill, sitting relaxed, climbing stairs, swimming, playing sports such as tennis, football, hockey, walking on high heels, playing for kids, or any other activity.

An angle indicator may be provided on the prosthesis 100, indicating at which angle the prosthesis joint part 220 may be positioned relative to the body joint part 210 for a particular activity.

The design of any part of the prosthesis 100 may be adapted to fit a particular user, adapting to for example the user's height, weight, any other parameter, or any combination thereof. Furthermore, some parts of the prosthesis 100 may be made to fit a specific purpose, such as running or swimming, or to fit a particular shoe, such as a sneaker, flip-flop, or high heel.

Any part of the foot prosthesis 300, such as the first curved strip 310, the second curved strip 320, and the heel part 330 may be manufactured as at least partially hollow parts. Furthermore, the components comprised by foot prosthesis 300 may comprise titanium, another metal, a resin, carbon, carbon fibre, Teflon, any other material, or any combination thereof, for example in the form of a composite. The materials comprised by the prosthesis 100 may be adapted to suit specific purposes, such as use in water.

A prosthesis 100 according to the second aspect allows, by virtue of the joint according to the first aspect, a rotation of the prosthesis joint part 220 relative to the body joint part 210 around the axis of rotation 201 by a certain amount of degrees. The amount of degrees which the prosthesis joint part 220 may be rotated relative to the body joint part 210 may thus be only limited by a first extreme position in which the heel mould 352 collides with the rear of the leg to which the body joint part 210 is attached. A second extreme position may be the position in which one of the foot mould 351, first straight section 312 or second straight section 322 collides with the front of the leg to which the body joint part 210 is attached.

When a user has found a particular amount of degrees of rotation between the prosthesis joint part 220 and the body joint part 210, due to the discrete first periodicity and the discrete second periodicity, the user is able to set this particular amount of degrees of rotation again after having changed the angle between the prosthesis joint part 220 and the body joint part 210. This reproducibility may be particularly advantageous for users who use the prosthesis 100 in different scenarios as discussed above.

In summary, a joint for a prosthesis is provided that comprises a prosthesis part and a body part. The two parts are connected by means of a connection part. A first pair of engaging sets of abutments is provided on the connection part and the prosthesis part and a second pair of engaging sets of abutments is provided on the connection art and the body part. By adjusting position of the connection part, the first pair of sets may be disengaged and by further adjusting the position, the second pair of sets may be disengaged too. This allows for adjustment of the joint at two levels. A prosthesis comprises two stripes of resilient material of which at least one has a curved part and a straight part. The joint is provided at a distal end, at the concave part of the strips. At straight parts, the strips cross and one strip extends beyond the other.

In the description above, it will be understood that when an element such as layer, region or substrate is referred to as being "on" or "onto" another element, the element is either directly on the other element, or intervening elements may also be present. Also, it will be understood that the values given in the description above, are given by way of example and that other values may be possible and/or may be strived for.

Furthermore, the invention may also be embodied with less components than provided in the embodiments described here, wherein one component carries out multiple functions. Just as well may the invention be embodied using more elements than depicted in the Figures, wherein functions carried out by one component in the embodiment provided are distributed over multiple components.

It is to be noted that the figures are only schematic representations of embodiments of the invention that are given by way of non-limiting examples. For the purpose of clarity and a concise description, features are described herein as part of the same or separate embodiments, however, it will be appreciated that the scope of the invention may include embodiments having combinations of all or some of the features described. The word 'comprising' does not exclude the presence of other features or steps than those listed in a claim. Furthermore, the words 'a' and 'an' shall not be construed as limited to 'only one', but instead are used to mean 'at least one', and do not exclude a plurality.

A person skilled in the art will readily appreciate that various parameters and values thereof disclosed in the description may be modified and that various embodiments disclosed and/or claimed may be combined without departing from the scope of the invention.

It is stipulated that the reference signs in the claims do not limit the scope of the claims, but are merely inserted to enhance the legibility of the claims.

The invention claimed is:

1. A joint for a prosthesis, comprising:
   a body joint part;
   a prosthesis joint part arranged to be connected to a prosthesis and to rotate relative to the body joint part around an axis of rotation;
   a connection part arranged to connect the body joint part and the prosthesis joint part;
   wherein
   one of the body joint part and a first side of the connection part is provided with a first set of abutments with a first periodicity;

the other of the body joint part and the first side of the connection part is provided with a third set of abutments arranged to engage with abutments of the first set of abutments;

one of the prosthesis joint part and side of the connection part is provided with set of abutments with periodicity;

the other of the prosthesis joint part and side of the connection part is provided with a fourth set of abutments arranged to engage with abutments of the second set of abutments; and the connection part is arranged to be translated between a first position, a second position, and a third position, wherein:
in the first position:
at least a part of the third set of abutments engages with at least a part of the first set of abutments; and
at least a part of the fourth set of abutments engages with at least a part of the second set of abutments;
in the second position:
at least a part of the third set of abutments engages with at least a part of the first set of abutments; and
the fourth set of abutments does not engage with the second set of abutments; and
in the third position:
the third set of abutments does not engage with the first set of abutments; and
the fourth set of abutments does not engage with the second set of abutments.

2. The joint according to claim 1, wherein:
the body joint part is provided with a first opening;
the prosthesis joint part is provided with opening;
the first opening and the second opening are aligned on the axis of rotation; and
the connection part is substantially cylindrical, and is arranged to at least be provided in the second opening.

3. The joint according to claim 2, wherein:
the first set of abutments is provided in the first opening of the body joint part;
the second set of abutments is provided in the second opening of the prosthesis joint part; and
the third set of abutments and the fourth set of abutments are provided on an outside of the connection part.

4. The joint according to claim 1, wherein:
at least one of the first set of abutments and the second set of abutments is conically shaped such that an outside diameter increases in the direction of the first position; and
at least one of the third set of abutments and the fourth set of abutments is conically shaped such that an outside diameter decreases in the direction of the first position.

5. The joint according to claim 1, wherein the connection element is arranged to be translated parallel to, and over, the axis of rotation between the first position, the second position, and the third position.

6. The joint according to claim 5, wherein the connection part is arranged to translate by sliding the connection part.

7. The joint according to claim 1, further comprising a first urging element with a first stiffness arranged to urge the connection part into the first position.

8. The joint according to claim 7, further comprising urging element with stiffness arranged to urge the connection part into the second position, wherein the first stiffness is lower than the second stiffness.

9. The joint according to claim 1, wherein the first periodicity and the second periodicity have no common denominator larger than 1.

10. A prosthesis, comprising the joint according to claim 1, wherein:
the body joint part is connected to a leg connection;
the prosthesis joint part is connected to a foot prosthesis;
the foot prosthesis comprises a first curved strip, including:
a first curved section; and
a first straight section, at a proximal end provided to the first curved section;
wherein:
the foot prosthesis is connected at a concave side of the first curved section to the prosthesis joint part; and
the foot prosthesis is arranged to bend resiliently.

11. The prosthesis according to claim 10, the prosthesis further comprising curved strip comprising curved section and straight section at a proximal end provided to the second curved section, wherein:
the second curved section at a concave side is connected to a convex side of the first curved section;
the second curved section crosses the first curved section at a crossing substantially at respectively a transition of the second curved section into the second straight section and a transition of the first curved section into the first straight section; and
a distal end of the first straight section and a distal end of the second straight section protrude substantially parallel.

12. The prosthesis according to claim 10, the foot prosthesis further comprising straight section, wherein:
the second straight section at a proximal end is attached to the first curved section; and
a distal end of the second straight section protrudes substantially parallel to the first straight section of the first curved strip.

13. The prosthesis according to claim 11, wherein the distal end of the first straight section protrudes further than the distal end of the second straight section.

14. The prosthesis according to claim 11, wherein the first curved strip is connected with the second curved strip substantially at the crossing.

15. The prosthesis according to claim 11, the foot prosthesis further comprising a heel part attached at a first end to the first curved strip.

16. The prosthesis according to claim 15, wherein the heel part at end is attached to the second curved strip.

17. The prosthesis according to claim 10, further comprising a mould of at least one of a foot, a heel and a sole.

* * * * *